United States Patent
Hayashi

[11] Patent Number: 5,904,899
[45] Date of Patent: May 18, 1999

[54] ASSAYING APPARATUS AND A VESSEL HOLDER DEVICE IN USE WITH THE ASSAYING APPARATUS

[75] Inventor: Hidechika Hayashi, Kanagawa, Japan

[73] Assignee: Tosoh Corporation, Shinnanyo, Japan

[21] Appl. No.: 09/079,184

[22] Filed: May 15, 1998

[30] Foreign Application Priority Data

May 15, 1997 [JP] Japan .................................. 9-125368
Jul. 18, 1997 [JP] Japan .................................. 9-193998

[51] Int. Cl.⁶ .................................................. G01N 35/02
[52] U.S. Cl. ............................ 422/65; 422/63; 422/102; 422/104; 436/43; 436/47; 436/48; 436/49
[58] Field of Search ............................... 422/63, 65, 102, 422/104; 436/43, 47, 48, 49; 206/446, 562, 563; 211/74

[56] References Cited

U.S. PATENT DOCUMENTS

| | | | |
|---|---|---|---|
| 3,883,306 | 5/1975 | Widen | 422/104 |
| 3,897,216 | 7/1975 | Jones | 422/65 |
| 3,916,157 | 10/1975 | Roulette et al. | 422/104 |
| 3,985,507 | 10/1976 | Litz et al. | 422/65 |
| 4,055,396 | 10/1977 | Meyer et al. | 422/104 |
| 4,322,216 | 3/1982 | Lillig et al. | 422/64 |
| 4,678,752 | 7/1987 | Thorne et al. | 435/291 |
| 4,727,032 | 2/1988 | Baisch et al. | 436/47 |
| 5,158,895 | 10/1992 | Ashihara et al. | 436/526 |
| 5,397,539 | 3/1995 | Hayashi et al. | 422/65 |
| 5,538,849 | 7/1996 | Uematsu et al. | 435/6 |
| 5,571,481 | 11/1996 | Powell et al. | 422/104 |
| 5,735,387 | 4/1998 | Polaniec et al. | 198/690.1 |

Primary Examiner—Long V. Le
Attorney, Agent, or Firm—Jacobson, Price, Holman & Stern, PLLC

[57] ABSTRACT

An apparatus has a holder unit for sample vessels and reaction vessels, a dispensing unit and a washing unit; wherein, (i) the holder unit involves a sample-vessel holder including a linear array of holes for receiving the sample vessels, a reaction-vessel holder including a linear array of holes for receiving the reaction vessels, a coupling arrangement for coupling together the sample-vessel holder and the reaction-vessel holder so that the linear arrays of the holes of the holders are arranged parallel to each other, and a moving arrangement for horizontally moving the coupled sample-vessel holder and the reaction-vessel holder, (ii) the dispensing unit is movable in the direction orthogonal to the horizontal-moving direction of the sample-vessel holder and the reaction-vessel holder, and (iii) the washing unit supplies cleaning liquid to the reaction vessels and absorbs the liquid-phase component from the reaction vessels.

15 Claims, 4 Drawing Sheets

ASSAYING APPARATUS AND A VESSEL HOLDER DEVICE IN USE WITH THE ASSAYING APPARATUS

BACKGROUND OF THE INVENTION

The present invention relates to an assaying apparatus which can be used in the field of biochemistry and immunochemistry, and a vessel holder unit in use with the assaying apparatus. More particularly, the present invention relates to a biochemistry and immunoassay apparatus, simple in construction and small in size, for handling samples, e.g., blood, serum, and urine, whose temperatures for storing them and for assaying them are different from each other, and also a small and simple vessel holder unit in use with the biochemistry and immunoassay apparatus.

In an immunochemical analysis apparatus, organism samples, e.g., serum, which are supplied in a state that those are contained in sample vessels, are transported to dispensing positions where the samples are dispensed by a dispensing device. The samples are absorbed from and discharged into reaction vessels into which a reagent necessary for reaction, e.g., a labeled antibody, which is transported in another route, has been put or is put anew. The resultant is placed under a temperature condition suitable for antigen-antibody reaction for a fixed period of time and then fluorescence emitted therefrom is measured.

In the immunoassay apparatus, it is a common practice that the sample vessels are transported to the dispensing positions (absorbing positions) where the sample dispensing is carried out by the dispensing device, while being held by hold/transporting member, such as a turn table, a snake chain, and a rack. On the other hand, the reaction vessels are usually transported to the dispensing positions (absorbing positions) where the sample dispensing is carried out by the dispensing device, while being held by hold/transporting member adjusted to a fixed temperature, such as a turn table, a snake chain, and a rack, or after the samples are dispensed, the reaction vessels are transported to the temperature adjusted hold/transported member. In a case where a reagent necessary for reaction is dispensed into the reaction vessels in the process of the immunoassay, a reagent vessel is held by the rack, for example, and the reagent is dispensed into the reaction vessel held by the turn table, for example, by use of the dispensing device.

Thus, in the conventional immunoassay apparatus, the sample vessels, the reaction vessels, and the reagent vessels are transported while being held by separate hold/transporting member, such as turn table, snake chain, rack and the like. For this reason, a plural number of hold/transporting member are included in one immunoassay apparatus. The construction causes the apparatus size to increase. Further, the dispensing device must be moved among those hold/transporting devices. This results in complexity of the moving mechanism.

In the conventional immunoassay apparatus that is increased in size and complicated in construction and operation, it is difficult to have an adjustment operation for adjusting each the devices which have been incorporated into the apparatus, and also to have an maintenance operation for the apparatus.

In addition to this, in some of the conventional immunoanalysis apparatus, the samples are not required to control in their temperature, the reaction vessels are usually subjected to a temperature adjustment, and only some type of reagents requiring their temperature adjustment are subjected to a temperature adjustment. Therefore, two temperature adjusting mechanism are required: one for the reaction-vessel holder and the other for the reagent-vessel holder. Further, in the case where both of the reagent vessel for the reagent requiring its temperature adjustment and the reagent vessel for the reagent not requiring its temperature adjustment are simultaneously utilized, the reagent-vessel holders must be provided for these reagent vessels, respectively.

SUMMARY OF THE INVENTION

Accordingly, it is an object of the present invention to provide a biochemical and immunoassay apparatus in which the moving mechanism for the sample vessels and the reaction vessels is simple, and the movement of the dispensing device is minimized.

In addition to this, it is an another object of the present invention is to provide a vessel holder device improved such that its construction is simple, the movement of the dispensing device is minimized, and such a temperature adjustment as to ensure a smooth execution of the immunoassay is realized by use of a single temperature adjusting mechanism.

The above-mentioned object of the present invention can attained by an assaying apparatus comprising:

a vessel holder unit for holding sample vessels containing samples and reaction vessels for antigen-antibody reaction, the vessel holder unit comprising;

a sample-vessel holder including a linear array of holes for receiving the sample vessels, a reaction-vessel holder including a linear array of holes for receiving the reaction vessels, and coupling means for coupling the sample-vessel holder and the reaction-vessel holder in such a manner that the linear arrays of the holes of the holders are arranged parallel to each other, horizontal moving means for horizontally moving a coupled unit of the sample-vessel holder and the reaction-vessel holder along the linear arrays of the holes;

a dispensing unit capable of absorbing liquid from the vessels and of discharging the liquid; and a washing unit for cleaning the inside of the reaction vessels, wherein the dispensing unit is movable in the direction orthogonal to the direction in which the coupled unit of the sample-vessel holder and the reaction-vessel holder is moved.

In the above-mentioned assaying apparatus, advantageously, the cleansing unit suppliable cleaning liquid to the reaction vessels, and absorbable a liquid-phase component from the reaction vessels.

In the thus constructed immunoassay apparatus, the dispensing unit may be formed with a dispensing nozzle, a pump for applying a positive/negative pressure to the dispensing nozzle, and a moving means for moving the nozzle in the direction, which is orthogonal to the moving direction of the vessels being moved by the vessel holder unit, and in the vertical direction. The nozzle is preferably of the type in which a dispensable tip is attached to the tip of the nozzle, and the dispensable tip is discarded after it is used. When this type of dispensable nozzle is used, it is possible to prevent the contamination of the samples. If means to clean the tip of the nozzle is used, a dispensable nozzle of the permanent type may be used with no problem. To secure a precise absorption and discharging the liquid, a volume pump, e.g., syringe pump and a plunger pump, is preferably used for the pump. The moving means may properly be constructed if it can move the dispensable nozzle on a horizontal plane in the direction that is orthogonal to the moving direction of the vessels being moved by the vessel holder unit, and in the vertical direction. In other words, the moving means may be constructed in any way if it can and absorb the liquid from and discharge it to all the vessels of the vessel holder unit in association with the movement of the vessels by the vessel holder unit. For the movement of the nozzle on the horizontal plane, the nozzle may be moved arcuately, for example. It is preferable to reciprocatively move the nozzle in the direction that is orthogonal to the moving direction of the vessels being moved by the vessel holder unit. The reason for this is that if the nozzle is so moved, it is easy to position the nozzle for the liquid absorbing and discharging.

The washing unit performs the cleaning, called B/F separation, in the heterogeneous immunoassay, and cleans the reaction vessels for the purpose of using them many times. The washing unit supplies a cleaning liquid to the reaction vessels and absorbs a liquid-phase component from the reaction vessels. To this end, the washing unit may be constructed with a cleaning probe for supplying a liquid-phase component to the reaction vessel and absorbing the same from the reaction vessel, moving means for inserting the cleaning probe into and pulling it out of the reaction vessel, a pump for supplying a cleaning liquid to the cleaning probe, a vacuum pump for absorbing the liquid-phase, a trap vessel for trapping the absorbed liquid-component, and the like.

Although in the embodiment the dispensing unit is movable in the vertical and horizontal directions, the washing unit is required to be movable only in the vertical direction.

In the above-mentioned assaying apparatus according to the present invention, advantageously further comprises:

temperature adjusting means for adjusting temperature of the reaction-vessel holder of the vessel holder unit within a predetermined range, wherein the sample-vessel holder is thermally isolated from an temperature adjusting function by the temperature adjusting means.

The definition of the above-mentioned apparatus is directed to a biochemistry and immunoassay apparatus in which a temperature adjustment is required for the reaction vessels, but it is not required for the sample vessels. The immunoassay apparatus includes temperature adjusting means for adjusting temperature of the reaction-vessel holder of the vessel holder unit to be within a range of temperature within which the antigen-antibody reaction may take place in the reaction vessels held by the reaction-vessel holder. In the immunoassay apparatus, the sample-vessel holder is thermally isolated from the temperature adjusting operation by the temperature adjusting means. The immunoassay apparatus thus constructed is capable of isolating a sample as an organism liquid, e.g., blood or serum from heat. In assaying such a sample as not to be affected by heat, there is no need of thermally isolating the sample vessels as described above. When a sample which is easily affected by heat is handled, the sample-vessel holder may be cooled. The temperature adjusting means attached to the reaction-vessel holder of the vessel holder unit may be constructed with the combination of a heater and a temperature sensor.

In the above-mentioned immunoassay apparatus according to the present invention, preferably, center-to-center distance between the adjacent holes of the sample-vessel holder and center-to-center distance between the adjacent holes of the reaction-vessel holder are made equal to each other, and the horizontal moving means can move the coupled unit of the sample-vessel holder and the reaction-vessel holder stepwisely by a predetermined interval equal to each the distance between the holes or a multiple of the distance through one operation of the horizontal moving moans. The immunoassay apparatus thus constructed have the following advantages. Both the sample-vessel and reaction-vessel holders of the vessel holder unit can be moved by use of one moving means, The moving operations, e.g., the control of their moving distance, are simplified.

In the vessel holder unit of the above-mentioned immunoassay apparatus according to the present invention, preferably, the coupling means couples the sample-vessel holder with the reaction-vessel holder such that the holes formed in the sample-vessel holder are aligned with the holes formed in the reaction-vessel holder when viewed in the direction that is orthogonal to the horizontal moving direction of the coupled unit. In the construction where both the sample- and reaction-vessel holders are thus coupled, it is easy to absorb the liquid from and discharge it into the sample and reaction vessels by merely constructing the dispensing unit so as to move reciprocatively. In particular in a case where the sample vessels and the reaction vessels are arranged in one-to-one correspondence, it is easy to control the movement of the dispensing unit as well as the vessel holder unit.

In the above-mentioned immunoassay apparatus according to the present invention, advantageously, at least one of the holes formed in the sample-vessel holder and the reaction-vessel holder is capable of holding reagent vessels containing reagents necessary for reactions. This technical feature eliminates the use of an additional vessel holder for holding the reagent vessels. In the above-mentioned immunoassay apparatus that the temperature adjusting means is attached to the reaction-vessel holder, and the sample-vessel holder is thermally isolated from the temperature adjusting means, the reagent vessel requiring its temperature adjustment is put in the hole of the reaction-vessel holder, and the reagent vessel not requiring the temperature adjustment is put in the hole of the sample-vessel holder. By so doing, there is no need of providing two temperature adjusting means.

As described above, the sample vessels, the reaction vessels, and the reagent vessels, if necessary, arc set in the vessel holder unit. The reagent may include a reagent of a type which should not be put into the reaction vessel in advance, and a reagent of another type in which it is unpreferable to put the reagent into the reaction vessel in advance. Those reagents are a substrate solution in the enzyme immunoassay and labeled antibodies in the 2-step immunoassay. The reagent vessel may be set in either the sample-vessel holder or the reaction-vessel holder. The reagent vessel containing a reagent requiring the temperature adjustment may be put in the reaction-vessel holder, and the reagent vessel containing a reagent which does not require the temperature adjustment or should avoid its temperature adjustment may be put in the sample-vessel holder.

In the above-mentioned immunoassay apparatus according to the present invention, advantageously, the reaction vessel contains ferrite, iron or magnetic stirrer pieces. Such a biochemistry and immunoassay apparatus may be provided with magnet oscillating means for applying an oscillating magnetic field to the reaction vessels, the oscillating means being located near the reaction-vessel holder of the vessel holder unit. In particular in performing the heterogeneous immunoassay, an insoluble carrier to which antibodies or antigens are bound are frequently used. In this case, ferrite, for example, may be built in the insoluble carrier.

Further, the above-mentioned another objection of the present invention can be achieved by a vessel holder device in use for an assaying apparatus, according to the present invention, comprising;

a sample-vessel holder including a linear array of holes for receiving the sample vessels, a reaction-vessel holder including a linear array of holes for receiving the reaction vessels, and coupling means for coupling the sample-vessel holder and the reaction-vessel holder in such manner that the linear arrays of the holes of the holders are arranged parallel to each other.

In the above-mentioned vessel holder device according to the present invention, advantageously, center-to-center distance between the adjacent holes of the sample-vessel holder and center-to-center distance between the adjacent holes of the reaction-vessel holder are equal to each other.

In the above-mentioned vessel holder device according to the present invention, advantageously, the coupling means couples the sample-vessel holder with the reaction-vessel holder such that the holes formed in the sample-vessel holder are aligned with the holes formed in the reaction-vessel holder when viewed in the direction that is orthogonal to the liner arrays of the holes.

Further, in the above-mentioned vessel holder device according to the present invention, advantageously, at least one of the holes formed in the sample-vessel holder and the reaction-vessel holder is capable of holding reagent vessels containing reagents necessary for reactions.

Furthermore, in the above-mentioned vessel holder device according to the present invention, advantageously, the coupling means comprises:

a spacer for defining an air layer between the sample-vessel holder and the reaction-vessel holder; and a bolt inserted into the spacer for securing the sample-vessel holder and the reaction-vessel holder.

Moreover, in the above-mentioned vessel holder device according to the present invention, advantageously, the spacer is made of polyacetal, and the bolt is made of a material of low thermal conductivity.

In a case where a temperature adjustment is required for the reaction vessels, but it is not required for the sample vessels, the reaction-vessel holder may include a temperature adjusting means for adjusting temperature of the reaction-vessel holder of the vessel holder unit to be within a range of temperature within which the antigen-antibody reaction may take place in the reaction vessels held by the reaction-vessel holder. Further, the sample-vessel holder is thermally isolated from the temperature adjusting operation by the temperature adjusting means.

In the vessel holder device thus constructed, distances each between the adjacent holes of the sample-vessel holder of the vessel holder unit are equal to each other at a fixed value of distance, and equal to those each between the adjacent holes of the reaction-vessel holder of the vessel holder unit, and the horizontal moving means is able to move the combination of the sample-vessel holder and the reaction-vessel holder a distance equal to or multiples of a distance equal to each the distance between the holes, through one operation of the horizontal moving means. The vessel holder device has the following advantages. Both the sample-vessel and reaction-vessel holders of the vessel holder unit can be moved by use of one moving means. The moving operations, e.g., the control of their moving distance, are simplified. In the vessel holder device, the coupling means couples the sample-vessel holder with the reaction-vessel holder such that the holes formed in the sample-vessel holder are aligned with the holes formed in the reaction-vessel holder when viewed in the direction that is orthogonal to the horizontal moving direction of the sample-vessel holder and the reaction-vessel holder. In the vessel holder device, the dispensing unit is reciprocatively movable in the direction orthogonal to the horizontal moving direction of the vessel holders, and the horizontal movement by the horizontal moving means is easy in its control.

The vessel holder device may be constructed such that some of the holes formed in the sample-vessel holder and/or the reaction-vessel holder are used for holding reagent vessels for containing reagents necessary for reactions.

However, a center-to-center distance between a sample-vessel an the reagent-vessel may be different from a center-to-center distance between the sample vessels. In addition, the center-to-center distance between the reaction-vessel and the reagent-vessel may be different from a center-to-center distance between the reaction vessels.

There is no need of using an additional vessel holder for holding the reagent vessels. In the above-mentioned construction that the temperature adjusting means is attached to the reaction-vessel holder, and the sample-vessel holder is thermally isolated from the temperature adjusting means, the reagent vessel requiring its temperature adjustment is put in the hole of the reaction-vessel holder, and the reagent vessel not requiring the temperature adjustment is put in the hole of the sample-vessel holder. By so doing, there is no need of providing two temperature adjusting means.

In a case where the reaction vessel contains ferrite, iron or magnetic stirrer pieces, magnet oscillating means for applying an oscillating magnetic field to the reaction vessels is preferably located near the reaction-vessel holder of the vessel holder unit.

DETAILED DESCRIPTION OF THE PREFERRED EMBODIMENTS

Embodiments of the present invention will be described in detail with reference to the accompanying drawings.

Figure 1:
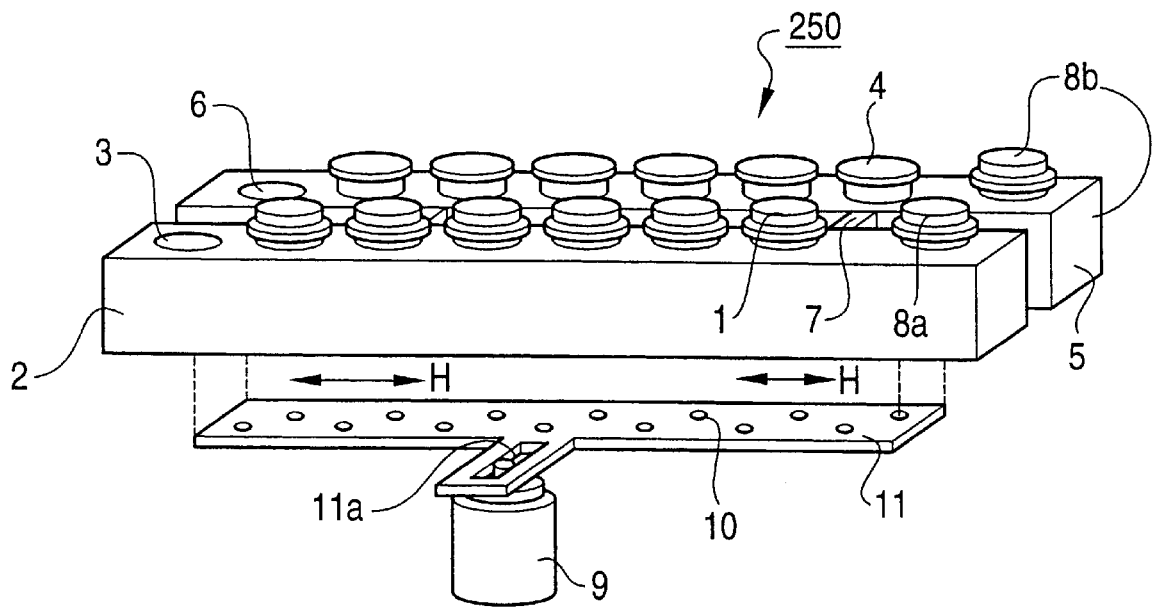
FIG. 1 is a perspective view showing vessel holder unit used for a biochemistry and immunoassay apparatus constructed according to the present invention.

Referring to FIG. 1, there is shown a vessel holder of a biochemistry and immunoassay apparatus (immunoanalysis apparatus) which uses reaction vessels, in a sealing manner, containing carriers (to which antibodies to antigens are bound) of synthetic resin containing ferrite built therein and another reagent, e.g., enzyme-labeled antibodies to antigens which have been lyophilized in advance. The reaction vessels are held on the holder after breaking the sealing of the reaction vessels.

In FIG. 1, reference numeral 1 is sample vessels for containing samples, e.g., serum; 2 is a sample-vessel holder for holding the sample vessels 1; 3 is sample-vessel holder holes formed in the sample-vessel holder 2; 4 is reaction vessels; 5 is a reaction-vessel holder for holding the reaction vessels 4; 6 is reaction-vessel holder holes formed in the reaction-vessel holder 5; 7 is coupling member for coupling together the sample-vessel holder 2 and the reaction-vessel holder 5; 8a is a first reagent vessel for containing a solution in which a lyophilized reagent, which does not require its temperature adjustment, is dissolved, and 8b is a second reagent vessel for containing an enzyme substrate liquid which requires its temperature adjustment, the first and second reagent vessels being generally designated by numeral 8; 9 is a motor; 9a is a drive shaft of the motor 9; 10 is a magnet; 11 is a magnet holding plate; 11a is an elongated hole of the magnet holding plate 11; and 250 is a vessel holder unit. Magnet oscillating member is made up of the motor 9, magnets 10 and magnet holding plate 11.

In the illustration of FIG. 1, the magnet holding plate 11 is disposed apart from the reaction-vessel holder 5. Actually, in order to ensure an efficient transmission of an oscillating magnetic field, those components are disposed close to each other, and a gap between them is preferably, set at 1 to 2 mm.

As shown in the FIG. 1, in this embodiment, the vessel holder unit 250 is capable of holding seven sample vessels 1, seven reaction vessels 4, and two reagent vessels 8. In case where the reagent vessels are not used, the vessel holder unit 250 may hold eight sample vessels and eight reaction vessels.

To be more specific, cups of polyethylene are used for the sample vessels 1 in the embodiment. The sample vessels 1 may also be cup-like vessels made of such a material (e.g., polypropylene or glass) as to be not changed in quality and nature when it comes in contact with a sample solution, or may be such a tubular member as a blood gathering tube, usually used. The sample-vessel holder holes 3, formed in the sample-vessel holder 2, are linearly arrayed as shown. The inside diameter and the depth of each of those sample-vessel holder holes 3 may properly be selected in accordance with the size and shape of the sample vessel 1 received thereby.

A cup made of polystyrene is utilized for each of the reaction vessels 4 in the embodiment.

On the other hand, the reaction vessels 4 may also be cup-like or tubular vessels made of such a material (e.g., polypropylene or glass) as to be not changed in quality and nature when it comes in contact with a sample solution. In a case where the contents of the reaction vessels 4 must be adjusted in temperature or stirred by the utilization of an oscillating magnetic field to be explained later, such a material as to exhibit a good thermal conductivity and a good magnetic permeability is used for the reaction vessels 4.

In this embodiment, part of a reagent necessary for the assay is put into each of those reaction vessels 4 in a sealing manner. The whole of the reagent, however, may be contained in advance sealingly.

The reaction vessels 4 is put on the reaction-vessel holder after breaking the sealing thereof.

A paramagnetism or antiferromagnetism material, e.g., ferrite or iron, may be contained in the reaction vessel in such a manner that the contents of the reaction vessel can be stirred by an oscillating magnetic field. Sometimes, a resin carrier insoluble in water is used in the immunochemical analysis. The resin carrier used in the invention may be a resin carrier containing magnetic material (stirrer tips) incorporated thereinto or a resin carrier incorporating ferrite powder thereinto (used in this embodiment).

The reaction-vessel holder holes 6, formed in the reaction-vessel holder 5, are linearly arrayed as shown. The inside diameter and the depth of each of those sample-vessel holder holes 3 may properly be selected in accordance with the size and shape of the reaction vessels 4 received thereby.

The sample-vessel holder 2 and the reaction-vessel holder 5 are made of aluminum in the embodiment. Of those holders, the sample-vessel holder 2 may be made of plastics or iron, if required. The sample-vessel holder 2 may be the block with holes as FIG. 1 or the U-shaped plate with upper holes as FIG. 3. In a case where the reaction-vessel holder 5 holds the reaction vessels 4 whose contents must be adjusted in temperature or stirred by an oscillating magnetic field to be explained later, the reaction-vessel holder 5 is preferably made of a material (e.g., aluminum) having a good thermal conductivity and a good magnetic permeability. Further, for the reaction-vessel holder holes 6, it is preferable that the inner wall of each reaction-vessel holder hole 6 is brought into tight-contact with the peripheral outer surface of the reaction vessel 4, and the bottom 6a of each reaction-vessel holder hole 6 is thin.

Figure 3:
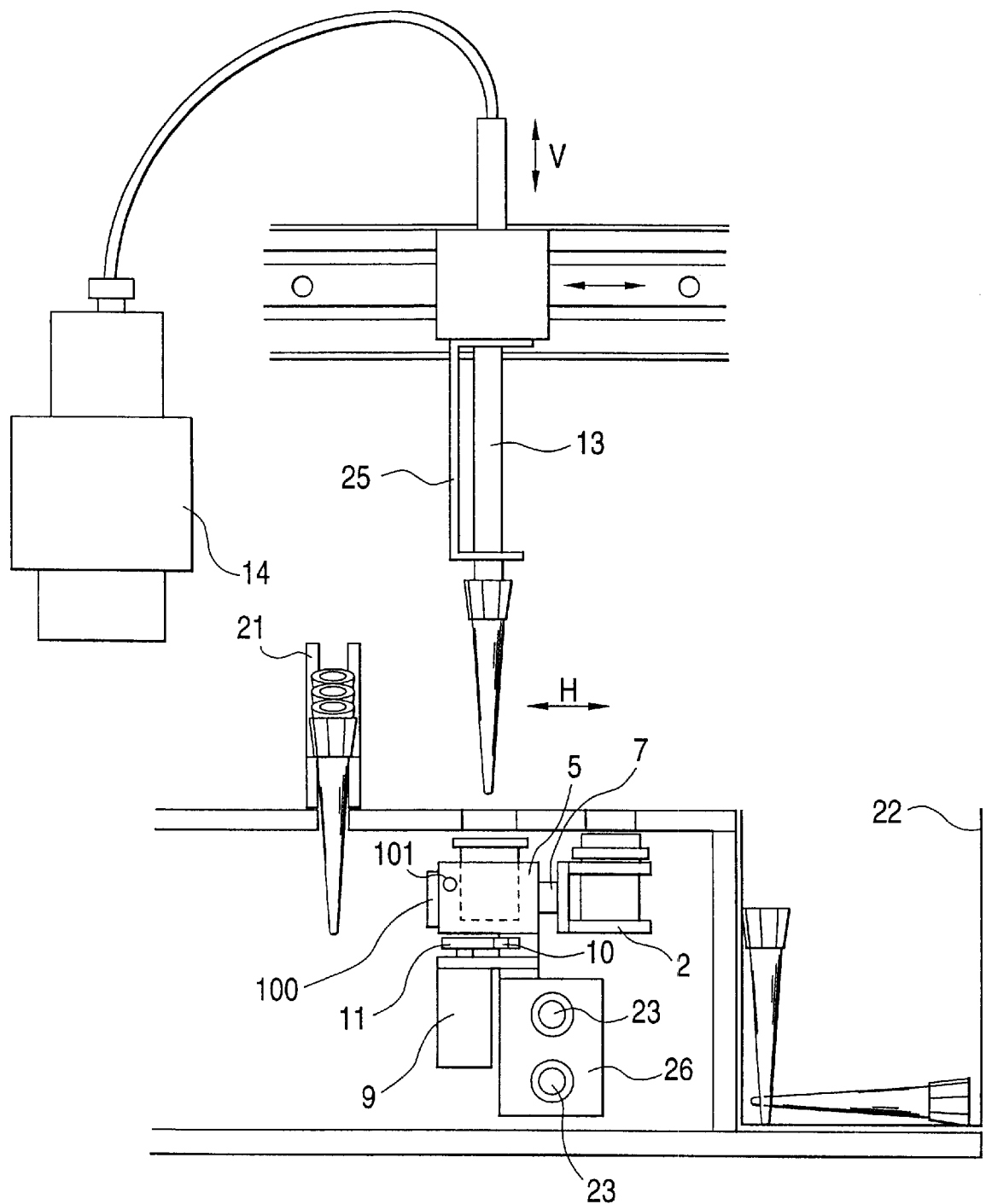
FIG. 3 is a side view showing a dispensing unit and its near structure in the immunoassay apparatus of FIG. 2.

In this embodiment, a heater 100, commercially available, is attached to the outer surface of the reaction-vessel holder 5 as shown in FIG. 3, and a temperature sensor 101 is attached to each reaction vessel. Temperature of the contents of the reaction vessel 4 are adjusted in a feedback manner by use of an output signal of the temperature sensor 101 attached thereto.

The magnet oscillating mechanism, which is made up of the motor 9, magnets 10 and magnet holding plate 11, is attached to the underside of the reaction-vessel holder 5. A disc (as a eccentric plate) with a protrusion (as a eccentric pin), which is eccentrically disposed, is attached to the motor 9. The magnets 10 are fastened to the magnet holding plate 11. The magnet holding plate 11, shaped like T, is fit to the protrusion of the disc, and is longitudinally movable when it is driven by the motor 9. While the magnet oscillating mechanism is attached to the reaction-vessel holder 5 in the present embodiment, it may be fixedly disposed under a path along which the reaction-vessel holder 5 is moved by a horizontal moving mechanism, with a small gap interposed therebetween.

Figure 4:
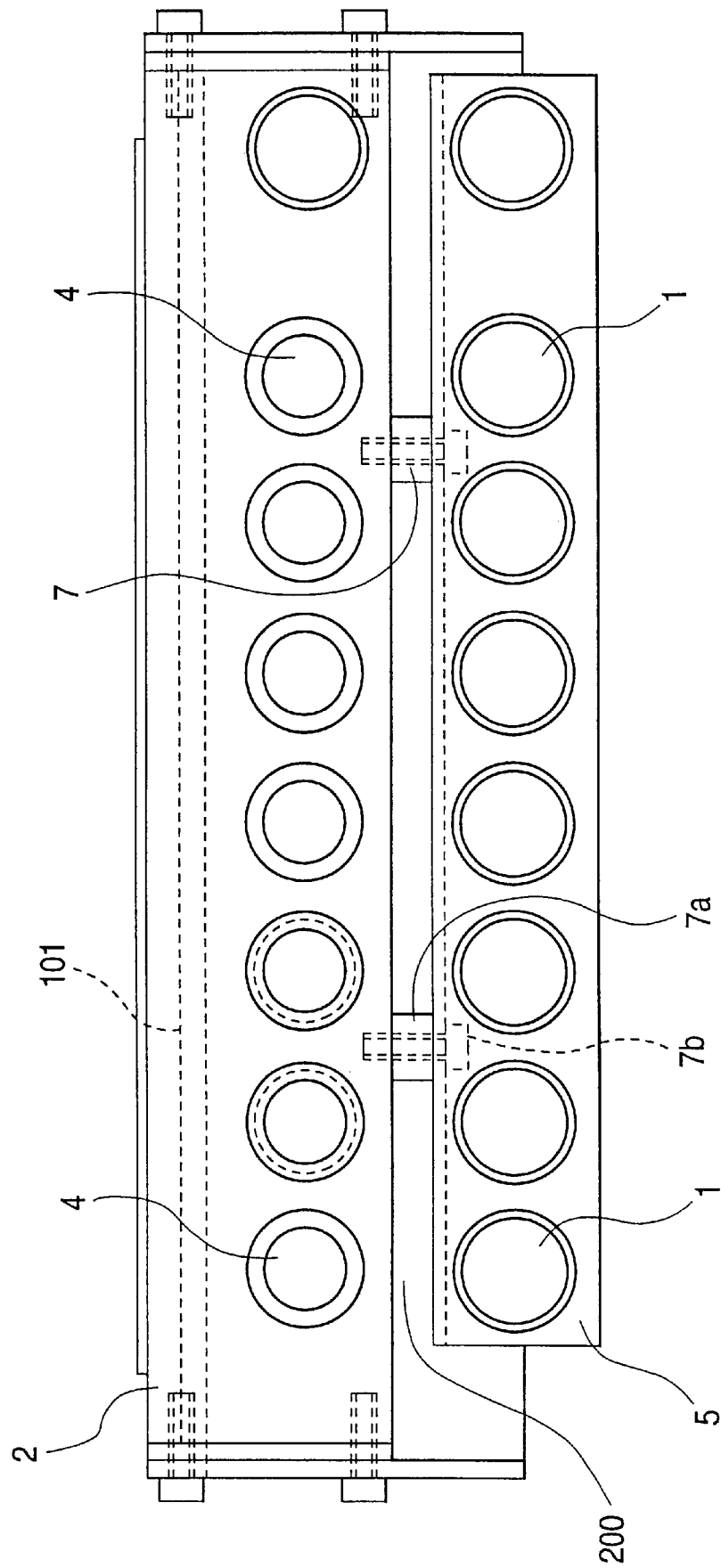
FIG. 4 is a plain view showing the vessel holder unit shown in FIG. 1.

The sample-vessel holder 2 and the reaction-vessel holder 5 are coupled together by the coupling member 7 in a state that the linear array of the sample-vessel holder holes 3 and that of the reaction-vessel holder holes 6 are arranged in parallel to each other. Both the holders are spaced from each other to such an extent that when the temperature adjustment for the reaction-vessel holder 5 is performed by use of temperature adjusting or control mechanisms equipped with a control unit, an air layer 200 (FIG. 4) being present between those holders prevents the temperature adjustment from affecting the samples contained in the sample vessels 1 of the sample-vessel holder 2. In the embodiment, the space between those holders is preferably set at 0.5 cm. By so spaced, there is no chance that the samples in the sample vessels 1 rise in temperature and are changed in quality, and hence an exact assay of them is ensured.

Each coupling members 7 is preferably formed with a spacer 7a and a bolt 7b (FIG. 5), in order to define the air layer 200 by securing such a state that the sample-vessel holder 2 and the reaction-vessel holder 5 are substantially uniformly spaced over their entire length by 0.5 cm, for example. The spacer 7a is made preferably of polyacetal, and the bolt 7b is made preferably of a material of low thermal conductivity.

In this embodiment, the air layer 200 is used for thermally insulating the sample-vessel holder 2 from the reaction-vessel holder 5. Any other suitable approach than this may be used for achieving the same purpose. For example, one approach is to coat those holders with thermal or heat insulating material, and another is to fill the space between those holders with heat insulating material.

Note that the air layer 200 per se can sufficiently impede the heat transmission, but there is a possible danger that heat is transferred through the movement of air. Hence, if it is significant to ensure a reliable thermal insulations the use of the thermal insulating material is preferable. Of course, sample-vessel holders may be cooled.

The heater 100 is preferably thin and long in order to uniformly heat the reaction vessel which is long and narrow. An insulated Nichrome (trade mark) wire rather than the bare one is preferably used for the heater 100 because some insulation measure must be taken in the case of the bare Nichrome wire. A narrow pipe-like sheath heater or a plate-like sheet heater may be used for the heater 100. The insulator of the sheet heater may be made of silicon rubber or polyimde. The sheet heater is approximately 0.5 mm to 1 mm thick and may take a proper shape. A lead wire for supplying electric power to the sheet heater may be attached to a proper position on the sheet heater.

In the present embodiment, a strip-like sheet heater covered with a silicon rubber is bonded to the outer surface of each reaction vessel 4 by adhesive. A double-coated tape, however, may be used for the bonding of the sheet heat.

Figure 2:
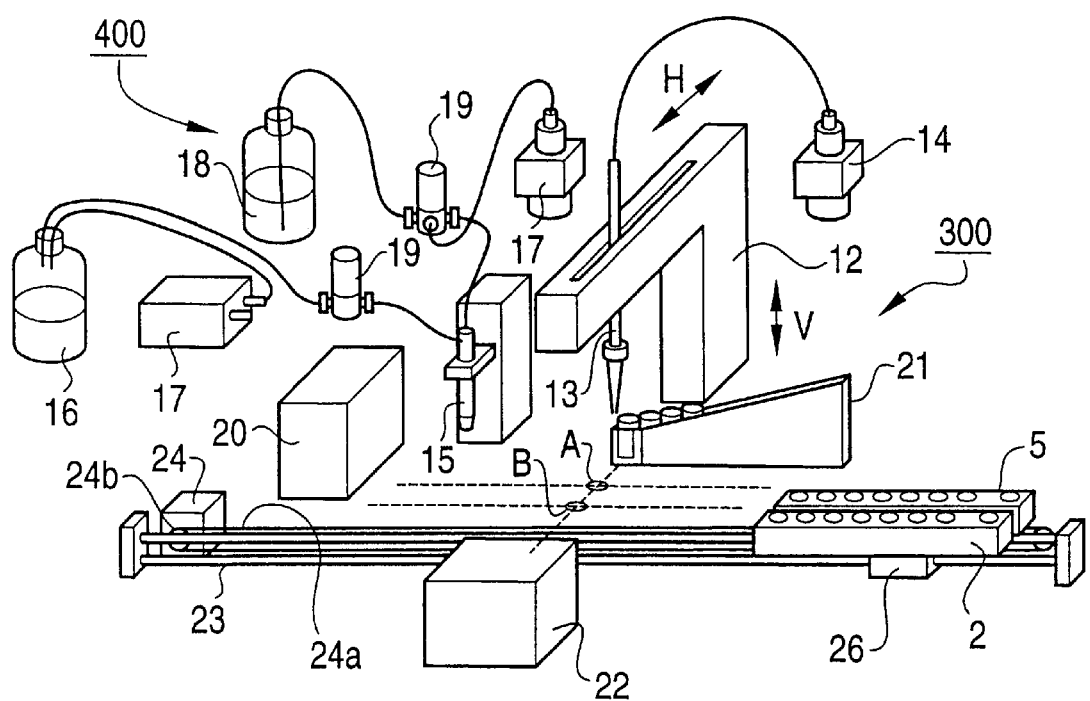
FIG. 2 is a perspective view showing the immunoassay apparatus of the invention when it is applied to an immune analysis.

As shown in FIG. 2, the horizontal moving mechanism is used for horizontally moving the combined unit of the sample-vessel holder 2 and the reaction-vessel holder 5, which are coupled together by the coupling member 7. The horizontal moving mechanism includes guide rails 23, a pulse motor 24, a belt 24a, pulleys 24b, and a carrier 26, fastened to the reaction-vessel holder 5, for carrying the combined unit of the sample-vessel holder 2 and the reaction-vessel holder 5. The pulse motor 24 is for generating a drive force to move the combined unit of the sample-vessel holder 2 and the reaction-vessel holder 5 along the guide rails 23.

As shown in FIGS. 2 and 3, the carrier 26 has a through-hole through which the guide rails 23 passes. All the vessels, which are held by the vessel holders of the vessel holder unit 250, may be moved to a washing unit 400 and a detecting members 20 by the horizontal moving mechanism.

In the vessel holder unit 250 shown in FIG. 1, the first and second reagent vessels 8a and 8b are put in and held by holes, which are exclusively used for receiving those reagent vessels, which are respectively formed in the sample-vessel holder 2 and the reaction-vessel holder 5 for containing reagents for the immunoanalysis.

There is a case where the outside diameters, shapes and the like of the reagent vessels are not acceptable by the holes formed in the sample- and reaction-vessel holders. One can easily deal with this problematic matter in a manner that the holes capable accepting those reagent vessels are additionally formed at proper locations lying on the prolongation of the linear arrays of the sample- and reaction-vessel holes formed in the related holders. The sample- and reaction-vessel holes may be used if those holes are altered so as to accept the reagent vessels, as a matter of course.

In the case where the number of kinds of reagents used is increased, another linear array of holes for receiving those reagent vessels may be formed in the sample- and/or reaction-vessel holder in parallel with the sample- and/or reaction vessel holes. Alternatively, a reagent vessel holder having a linear array of holes for receiving those reagent vessels may additionally be used while those vessel holders are coupled together by coupling member. In this case, a total number of vessel holders used is three.

Note that it is a preferable construction that the center-to-center distance between the adjacent sample vessel holes, the center-to-center distance between the adjacent reagent vessel holes, in such a manner that the movement of the sample-vessel and reaction-vessel holders by the horizontal moving mechanism is made simple and easy.

In a case where the center-to-center distance between the adjacent sample vessel holes is equal to that between the adjacent reaction vessel holes, but different from that between the sample-vessel hole and the reagent-vessel holes (for example, the distance of the sample-vessels hole and the reagent-vessel holes is about 1.5 times as large as that of the former), or that between the reaction-vessel hole and the reagent-vessel hole as in the illustrated case (in particular FIG. 4), the horizontal moving mechanism for the sample-vessel and reaction-vessel holders is adjusted so that the agent, reaction solution and the reagent can be dispensed into all the vessels.

Two types of reagent vessels, the first reagent vessel 8a for containing a solution in which a lyophilized reagent, which does not require its temperature adjustment, is dissolved, and the second reagent vessel 8b for containing an enzyme substrate liquid which requires its temperature adjustment, are used in the embodiment. If required, another type of reagent vessel may be used, which contains a diluent for diluting a sample, called a second reagent (enzyme labeled antibody), as another kind of reagent not requiring a temperature adjustment.

The immunoassay apparatus incorporating the present invention is illustrated overall in FIG. 2. As shown, the immunoassay apparatus includes a dispensing unit 300 and a washing unit 400. The dispensing unit 300 is made up of an L-shaped nozzle support or arm 12, a dispensing nozzle 13 and a pumping member or a plunger pump 14. The L-shaped nozzle support 12 supports the dispensing nozzle 13 in the vertical and horizontal directions (V and H); as shown in FIG. 3, the vertical direction (V) is orthogonal to the plane including the moving direction (with arrows) of the horizontal moving mechanism, and the horizontal direction (H) is along the plane including that moving direction but is orthogonal to the moving direction. The pumping member 14 functions to absorb the liquid from and discharge it to a disposable tip (to be described later) attached to the nozzle tip. The washing unit 400 as a B/F washing unit is made up of a cleaning probe 15, a used liquid receptacle 16, pumps 17, a cleaning liquid container 18, and electromagnetic valves 19. In FIG. 2, reference numeral 20 is a detecting member; 21 is a tip holder member for supplying disposable tips to the dispensing nozzle 13; and 22 is a waste box 22 into which used disposable tips are discarded. In the embodiment, the disposable tips after used are discarded to prevent contamination of the samples. To contain the used disposable tips, the waste box 22 is used.

For the immunochemical analysis, the immunoassay apparatus includes the cleaning probe 15 (called as B/F separation member) for removing a labeled reagent which does not form an immune complex of antigen-antibody, for example, and the detecting member 20 for detecting a quantity of a labeled reagent which forms an immune complex. The B/F separation member 15 is communicatively connected to the cleaning liquid container 18 and the electromagnetic valves 19.

The detecting member 20 may properly be selected in accordance with the immunoassay method used. Some immunoassay methods are enumerated below.

A first immunoassay is that an antibody, for example, is directly bound (labeled) to a dye having the nature of light absorption or of emitting fluorescence, and absorption or fluorescence of an immune complex of antibody and antigen, which is caused by an antigen-antibody reaction, is measured.

A second immunoassay is that an antibody, for example, is directly bound (labeled) to a dye having the nature of chemiluminescence, a reagent for triggering luminescence, e.g. acid or alkali, is added to an immune complex of antibody and antigen, which is caused by an antigen-antibody reaction, and the resultant luminescence is measured.

A third immunoassay is that an antibody, for example, is directly bound (labeled) to enzyme, an enzyme substrate is added to an immune complex of antibody and antigen, which is caused by an antigen-antibody reaction, and the resultant absorption, fluorescence or luminescent material is measured.

One may select a proper detecting member in consideration with the measurable nature of an object to be assayed. The detecting method is not limited in particular. A detecting method that may be used in the invention is that fluorescence is obtained by projecting an exciting light on the upper surface of the reaction vessel by use of a dichroic mirror, for example. Another detecting method is that a liquid-phase component is absorbed from the reaction vessel and fed to a flow cell, whereby a flow detection is performed. A method may be used in which a fluorescence detecting member is fixed, and the reaction vessel is moved to the fluorescence detecting member by use of the moving mechanism of the vessel holder unit. Additionally, the detecting member may be installed movably, like the dispensing unit.

The dispensing nozzle 13 with a disposable tip attached to the tip thereof in the dispensing unit 300 is supported by the arm 12, which is horizontally and vertically movable, and is communicatively coupled with the plunger pump 14 by Teflon (Trade Mark) piping. The tip of the dispensing nozzle 13 is shaped so as to be fit into the opening of the disposable tip, The nozzle is set to the tip by pushing the tip of the nozzle into the opening of the tip. A nozzle removal tool 25 in FIG. 3 is attached to the dispensing nozzle 13. A used disposable tip is detached from the nozzle above the waste box 22 by the nozzle removal tool 25.

The immunoassay apparatus has a double-stage structure; a first stage includes the L-shaped nozzle support 12, tip holder member 21, detecting member 20 and waste box 22, and a second stage, located under the first stage, includes the vessel holder unit. Through-holes A and B are provided which interconnect the first and second stages. To absorb samples, for example, from the sample, reaction and reagent vessels, the dispensing nozzle 13 is made to descend, through the through-holes, to the sample vessels or the reagent vessel (through-hole B) or to the reaction vessels or the reagent vessel (through-hole A).

Turning now to FIG. 3, there is shown the dispensing unit and its near structure. The nozzle removal tool, designated by numeral 25, for detaching a used disposable tip from the dispensing nozzle 13 is attached to the dispensing nozzle per se, as shown. The dispensing nozzle 13, as shown, is movable in the vertical direction (V), which is vertical orthogonal to the plane including the moving direction (with arrows) of the horizontal moving mechanism, and also in the horizontal direction (H), which is along the plane including that moving direction but is orthogonal to the moving direction.

Description will be given about a heterogeneous immunoassaying method using reaction vessels, in a sealing manner, containing carriers to which antibodies are bound (magnetic carriers containing ferrite built therein) and another reagent, e.g., enzyme-labeled antibodies to antigens is which have been lyophilized.

The sample vessels 1 containing samples to be assayed, e.g., human serums, are placed in the related holes of the sample-vessel holders 2 of the vessel holder unit 250, and a number of reaction vessels 4, equal to the number of samples, are placed in the related holes of the reaction-vessel holder 5. A solution for dissolving the lyophilized materials in the reaction-vessel holders 2 is put into the sample-vessel holder holes 3 of the sample-vessel holder 2, and an enzyme substrate is put into the reaction-vessel holder holes 6 of the reaction-vessel holder 5.

The moving mechanism of the dispensing member and the vessel holder unit are controlled in such a manner that predetermined amounts of samples and a predetermined amount of solution are dispensed into those reaction vessels 4. Every time the dispensing of the samples and solution is finished, the used dispensable tips are discarded, and new ones are attached to the dispensing nozzle 13 in preparation for the next dispensing operation.

The reaction temperature affects the antigen-antibody reaction. Therefore, the temperature of the reaction vessels 4 containing the samples and the solution are controlled so as to be a predetermined reaction temperature, while antigen-antibody reaction progresses for a predetermined time so as to form immune complexes on the carrier surfaces. After the predetermined time elapses, the washing unit 400 and the vessel holder unit 250 are controlled, and the reaction vessels 4 are cleaned several times. The carriers are not discarded out of the reaction vessels 4 through the cleaning operation by the washing unit 400.

After the cleaning is completed, a predetermined amount of substrate liquid is transferred from the reagent vessels 86 to the reaction vessels 4 by controlling the washing unit 400 and the vessel holder unit 50. The substrate may be 4-methylumbelliferyl phosphoric acid when the enzyme used for the label is alkaline phosphatase. The dispensed substrate receives an action by the enzyme of the immune complex, and is transformed into a material emitting fluorescence, for example.

Finally, the reaction vessels 4 are transported to the detecting member by controlling the vessel holder unit 250, and absorption, fluorescence, luminescence, and the like are detected by the detecting member.

Figure 5:
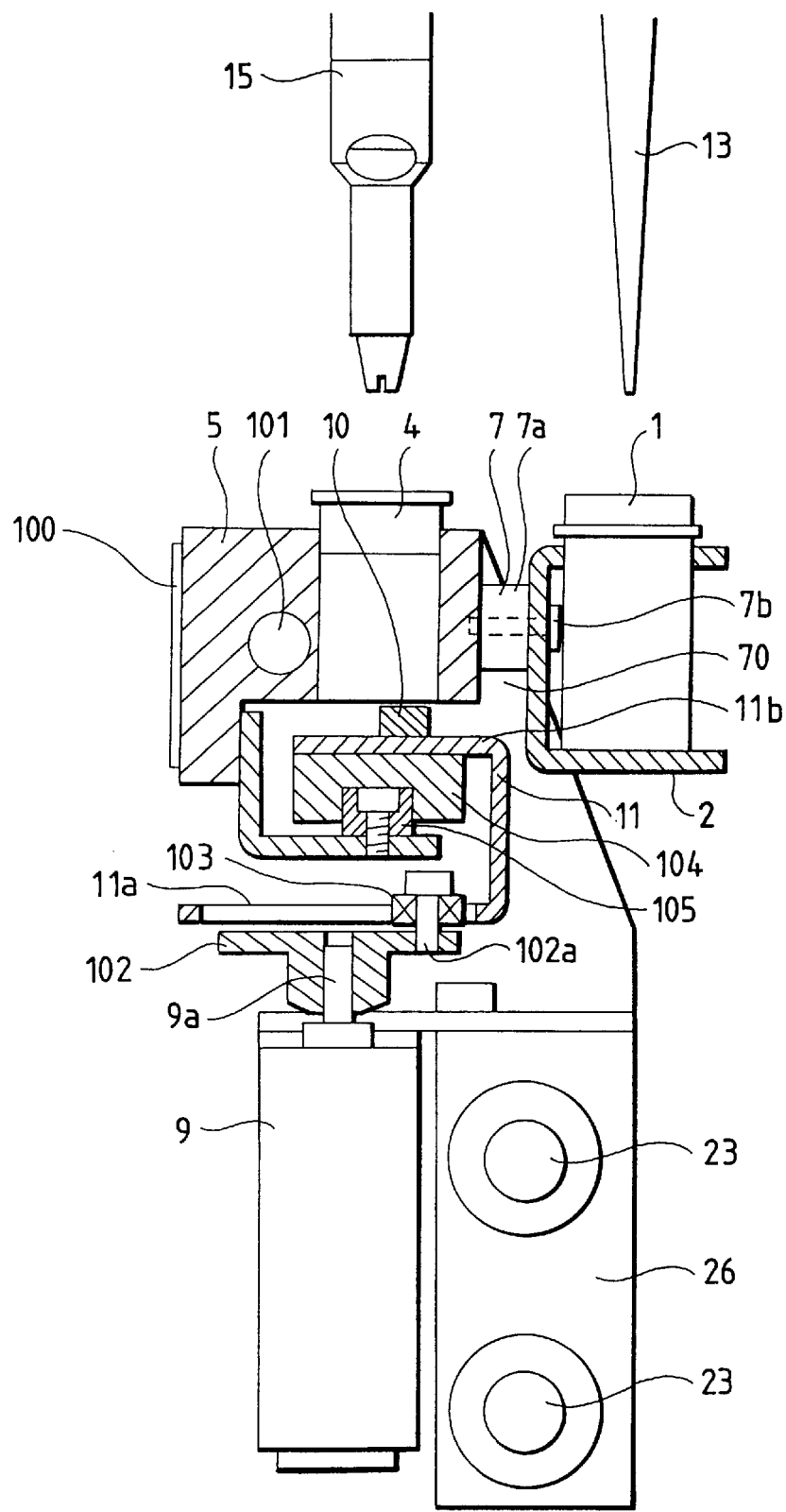
FIG. 5 is a side and cross sectional view showing a modification of the dispensing unit and its near structure in the immunoassay apparatus of FIG. 3.

FIG. 5 is a side and cross sectional view showing a modification of the dispensing unit and its near structure, particularly a magnet oscillating mechanism including the magnet holding plate, in the immunoassay apparatus of FIG. 3. In the description in connection with FIG. 5, like reference numerals are used for designating like or equivalent portions in FIG. 3.

Reference numerals and their denotations in FIG. 5 are: 9a is a drive shaft; 11a is an elongated hole; 11b is an upper plate; 102 is an eccentric plate; 102a is an eccentric pin; 103 is a bearing; 104 is a linearly driven slider; and 105 is a rail.

As shown in FIG. 5, the eccentric plate 102 is fastened to the drive shaft 9a of the motor 9 while being coaxial with the latter. The eccentric pin 102a stands erect on the eccentric plate 132 at a position set off from the drive shaft 9a of the motor 9. The bearing 103 is firmly attached to the tip of the eccentric pin 102a. The bearing 103 is slidably inserted into the elongated hole 11a formed in the magnet holding plate 11 shaped like U in cross section. The elongated hole 11a is shaped as shown in FIG. 1.

The magnets 10 are mounted on the upper surface of the upper plate 11b of the magnet holding plate 11 in a zig-zag fashion (as shown in FIG. 1). The linearly driven slider 104 is slidably attached to the underside of the magnet holding plate 11 while being elongated in the direction of feeding the sample-vessel holder 2, viz., in the direction vertical to the drawing surface of FIG. 5. The rail 105 for guiding the linearly driven slider 104 is disposed under the reaction-vessel holder 5 and also elongated in the same direction as of the linearly driven slider 104.

The operation of the magnet oscillating unit thus constructed will be described.

The motor 9 is driven and the eccentric plate 102 is turned, the eccentric pin 102a of the eccentric plate 102 revolves around the drive shaft 9a of the motor 9. The bearing 103 fastened to the eccentric pin 102a reciprocatively moves the magnet holding plate 11 in the moving directions of the sample-vessel holder 2. The reason for this is that the moving directions of the magnet holding plate 11 is regulated by the rail 105 and the linearly driven slider 104, and the bearing 103 reciprocatively moves within the elongated hole 11a of the magnet holding plate 11.

To stir the sample particles in the reaction vessels 4, the magnets 10, which are arrayed on the magnet holding plate 11 located under the sample-vessel holder 2, are oscillated preferably 60 to 120 times per minute and at about 18 mm in amplitude.

The structure to oscillate the magnet holding plate 11 is not limited to the above one, but may take any form if it is capable of oscillating (vibrating) the magnets 10 under the reaction vessels 4, as a matter of course.

The useful effects of the immunoassay apparatus constructed as mentioned above will be described. The sample vessels and the reaction vessels, and if necessary, the reagent vessels may be held by a single vessel holder unit, which is movable in unit and constructed in a thermally insulated manner. On the other hand, those types of vessels are separately held by their own vessel holder units in the conventional immunoassay apparatus. In this respect, the moving mechanism of the immunoassay apparatus of the invention is more simplified in construction than that of the conventional immunoassay apparatus. Further, the immunoassay apparatus of the invention is small in size and easy in its maintenance. Further, it is noted that the respective units are linearly and reciprocatively moved. This accrues simplification of the construction and reduction of cost to manufacture.

With such a feature that the sample vessels and the reaction vessels, and if necessary, the reagent vessels may be held by a single vessel holder unit, which is movable in unit and constructed in a thermally insulated manner, the vessel holder device is reduced in size, and the immunoassay apparatus is reduced in size if it is assembled into the apparatus. To absorb and discharge the samples and the like contained in the vessels held by the vessel holder device, the dispensing unit is moved in the vertical and horizontal moving directions of the vessel holder device. This feature bring about construction simplicity and size reduction of the moving mechanism.

In Addition, in a case where the reagent requiring its temperature adjustment and that not requiring the same are both used, it is only needed that a single temperature adjusting mechanism is used While there has been described in connection with the preferred embodiment of the invention, it will he obvious to those skilled in the art that various changes and modifications may be made therein without departing from the invention, and it is aimed, therefore, to cover in the appended claim all such changes and modifications as fall within the true spirit and scope of the invention.

What is claimed is:

1. An assaying apparatus comprising:
a vessel holder unit (250) for holding sample vessels containing samples and reaction vessels for antigen-antibody reaction, said vessel holder unit comprising;
a sample-vessel holder (2) including a linear array of holes (3) for receiving said sample vessels,
a reaction-vessel holder (5) including a linear array of holes (6) for receiving said reaction vessels, and
coupling means (7) for coupling said sample-vessel holder (2) and said reaction-vessel holder (5) in such a manner that the linear arrays of said holes (3, 6) of said holders (2, 5) are arranged parallel to each other,
horizontal moving means (23, 24, 24a, 24b, 26) for horizontally moving a coupled unit of said sample-vessel holder and said reaction-vessel holder along the linear arrays of said holes;
a dispensing unit capable of absorbing liquid from the vessels and of discharging the liquid; and
a washing unit for cleaning the inside of the reaction vessels,
wherein said dispensing unit is movable in a direction orthogonal to the direction in which the coupled unit of said sample-vessel holder and said reaction-vessel holder is moved.

2. The assaying apparatus according to claim 1, wherein said washing unit suppliable cleaning liquid to said reaction vessels, and absorbable a liquid-phase component from said reaction vessels.

3. The assaying apparatus according to claim 1, further comprising:
temperature adjusting means (100) for adjusting temperature of said reaction-vessel holder of said vessel holder unit within a predetermined range,
wherein said sample-vessel holder is thermally isolated from a temperature adjusting function by said temperature adjusting means.

4. The assaying apparatus according to claim 1, wherein center-to-center distance between said adjacent holes of said sample-vessel holder and center-to-center distance between said adjacent holes of said reaction-vessel holder are equal to each other, and said horizontal moving means movable the coupled unit of said sample-vessel holder and said reaction-vessel holder stepwisely by a predetermined interval equal to each said distance between said holes or a multiple of said distance through one operation of said horizontal moving means.

5. The assaying apparatus according to claim 4, wherein in said vessel holder unit, said coupling means couples said sample-vessel holder with said reaction-vessel holder such that said holes formed in said sample-vessel holder are aligned with said holes formed in said reaction-vessel holder when viewed in a direction that is orthogonal to the horizontal moving direction of said coupled unit.

6. The assaying apparatus according to claim 4, wherein at least one of said holes formed in said sample-vessel holder and said reaction-vessel holder is capable of holding reagent vessels containing reagents necessary for reactions.

7. The assaying apparatus according to claim 1, further comprising:

magnet oscillating mean located near said reaction-vessel holder for applying an oscillating magnetic field to said reaction vessels.

8. The assaying apparatus according to claim 1, wherein said coupling means (7) comprises:

a spacer (7a) for defining an air layer (200) between said sample-vessel holder (2) and said reaction-vessel holder (5); and a bolt (7b) inserted into said spacer (7a) for securing said sample-vessel holder (2) and said reaction-vessel holder (5).

9. The assaying apparatus according to claim 8, wherein said spacer (7a) is made of polyacetal, and said bolt (7b) is made of a material of low thermal conductivity.

10. A vessel holder device in use for an assaying apparatus comprising:

a sample-vessel holder (2) including a linear array of holes (3) for receiving said sample vessels, a reaction-vessel holder (5) including a linear array of holes (6) for receiving said reaction vessels, coupling means (7) for coupling said sample-vessel holder (2) and said reaction-vessel holder (5) in such a manner that the linear arrays of said holes (3, 6) of said holders (2, 5) are arranged parallel to each other, and temperature adjusting means (100) for adjusting temperature of said reaction-vessel holder of said vessel holder unit within a predetermined range, wherein said sample-vessel holder is thermally isolated from a temperature adjusting function by said temperature adjusting means.

11. The vessel holder device according to claim 10, wherein center-to-center distance between said adjacent holes of said sample-vessel holder and center-to-center distance between said adjacent holes of said reaction-vessel holder are equal to each other.

12. The vessel holder device according to claim 10, wherein said coupling means couples said sample-vessel holder with said reaction-vessel holder such that said holes formed in said sample-vessel holder are aligned with said holes formed in said reaction-vessel holder when viewed in a direction that is orthogonal to said liner arrays of said holes.

13. The vessel holder device according to claim 10, wherein at least one of said holes formed in said sample-vessel holder and said reaction-vessel holder is capable of holding reagent vessels containing reagents necessary for reactions.

14. The vessel holder device according to claim 10, wherein said coupling means (7) comprises:

a spacer (7a) for defining an air layer (200) between said sample-vessel holder (2) and said reaction-vessel holder (5); and a bolt (7b) inserted into said spacer (7a) for securing said sample-vessel holder (2) and said reaction-vessel holder (5).

15. The vessel holder device according to claim 14, wherein said spacer (7a) is made of polyacetal, and said bolt (7b) is made of a material of low thermal conductivity.

* * * * *